United States Patent [19]

Hargest, III

[11] 4,333,454
[45] Jun. 8, 1982

[54] AUTOMATIC TUBULAR FEEDING APPARATUS AND METHOD

[76] Inventor: Thomas S. Hargest, III, 1078 Winslow Dr., Charleston, S.C. 29412

[21] Appl. No.: 111,609

[22] Filed: Jan. 14, 1980

[51] Int. Cl.³ .............................................. A61M 5/00
[52] U.S. Cl. ................................ 128/214 R; 222/133; 222/145
[58] Field of Search ........... 128/214 R, 214 C, 214 E, 128/214 F; 137/209; 222/133, 134, 145

[56] References Cited

U.S. PATENT DOCUMENTS

| | | | |
|---|---|---|---|
| 1,084,753 | 1/1914 | Owens | 222/145 |
| 2,508,762 | 5/1950 | Lapple | 222/133 |
| 2,946,488 | 7/1960 | Kraft | 222/134 |
| 3,251,508 | 5/1966 | Borys | 222/145 |
| 3,886,937 | 6/1975 | Bobo et al. | 222/145 |
| 3,896,733 | 7/1975 | Rosenberg | 128/214 R |
| 3,993,066 | 11/1976 | Virag | 128/214 C |
| 4,099,527 | 7/1978 | Howell | 128/214 C |
| 4,180,068 | 12/1979 | Jacobsen et al. | 128/214 R |
| 4,223,695 | 9/1980 | Muetterties | 128/214 R |

Primary Examiner—Gene Mancene
Assistant Examiner—John J. Wilson
Attorney, Agent, or Firm—Wellington M. Manning, Jr.; Luke J. Wilburn, Jr.

[57] ABSTRACT

A system for sequential tubular administration of first and second fluids including a first reservoir to contain a first solution, e.g., a solution of medication; a second reservoir having less capacity than the volume of solution in the first reservoir with an overflow chamber. The two reservoirs are in communication with each other, and both are provided with valved solution discharge lines, the entrance to which is provided with a ball float valve. The two discharge lines meet at a wye connection having an infusion feed assembly at an outer free end of same. With a first solution in the first reservoir and with both reservoirs closed to the atmosphere, second solution, e.g., I.V. solution may be fed into the second reservoir which displaces air therefrom into the first reservoir to assist in feeding solution from the first reservoir. Just prior to completion of discharge of solution from the first reservoir, solution from the second reservoir overflows into the overflow chamber, opens a ball float valve and initiates administration of the second solution upon completion of administration of the first solution. Both solution discharge lines are adjustable for flow rate and provided with off-on connections and check valves. Automatic switching to administration of second solution upon completion of administration of the first solution precludes the administration of air into the line and prevents blockage of the infusion feed assembly by clotting of blood, etc. therein.

27 Claims, 3 Drawing Figures

AUTOMATIC TUBULAR FEEDING APPARATUS AND METHOD

BACKGROUND OF THE INVENTION

The positive influence of intravenously feeding fluids to a patient over prescribed periods of time have been recognized by the medical profession. Further, while in a conventional sense glucose or the like is intravenously fed to a patient through a cannula assembly, many arrangements have heretofore been suggested and employed where a plurality of fluids are intravenously fed to a patient, either simultaneously or in a prescribed sequential fashion.

In the development of the multiple feeding systems, arrangements have been provided whereby a plurality of containers have been connected to a single cannula assembly via a wye connection or the like. Conventionally, this has been referred to as a piggy back arrangement, where one of the bags may be suspended at an elevation greater than the other. In certain arrangements where multiple fluids are administered to a patient, one of the fluids constitutes medication where the medicine has been premixed with distilled water, saline solution or the like, while the other fluid is a conventional I.V. fluid such as a saline solution, glucose or the like. In utilizing these systems, the medication fluid is administered at a particular rate in accordance with the requirements of medical personnel. Since the unit, when used, is normally employed over protracted periods of time for a single patient after which it is discarded, it is quite beneficial that the system remain viable for periodic administration of medication. Normally therefore, with knowledge of the volume of medication fluid to be administered and the rate of administration, a nurse can calculate the time required for administration of the medication, and return to the patient's room at the appropriate time to switch flow from the medication leg of the wye to flow of I.V. fluid which precludes the introduction of air into the system and also very importantly precludes clotting of blood and therefore blockage in and around the cannula assembly which would necessitate the use of a new assembly that must again be inserted into the patient's vein, which of course is both costly and cause discomfort to the patient.

A primary concern in the normal arrangement, if not the most important concern, is the requirement that medical personnel be in attendance to switch over from administration of medication to the I.V. fluid. Not only is the arrangement problematical due to human error or forgetfulness, but the arrangement also intensifies the need for additional medical personnel proximate to where the fluids are being administered, and often presents problems where nurses or other medical personnel are needed at more than one location at the same time.

A great deal of development effort has been expended in the area of improving the system described above by way of the use of audible alarms to indicate cessation of medication or I.V. flow; the use of positive driven pumps to control the rate of fluid flow through the system; the use of certain switching arrangements where pressure variation in the system would automatically cause valves to open or close and the like, all of which are directed to reducing the time required by medical personnel in administering the medication and switching to the I.V. fluid, while not detracting from patient comfort, or increasing the probability of air entering the system or clotting of the infusion assembly.

Certain prior art patents are directed to arrangements for improving the intravenous feeding apparatus as exemplified by U.S. Pat. No. 2,999,499; 3,216,419; 3,521,635; 3,543,752; 3,756,237; 3,776,229; 3,886,937; 3,929,157; 3,931,818; 3,967,620; 3,982,534; 4,000,738; 4,010,750; 4,037,596; 4,056,333; 4,096,879; 4,099,527; 4,103,686; 4,137,915; and 4,146,028.

The apparatus and method of the present invention represents an improvement over systems heretofore devised, in that, the present system provides automatic switch over upon cessation of a first fluid flow to a second fluid flow without presence of a nurse or other attendant in virtually a fail safe fashion. The known prior art as set forth above is not believed to either anticipate or suggest the apparatus or method of the present invention.

SUMMARY OF THE INVENTION

It is an object of the present invention to provide an improved tubular feeding apparatus that will automatically switch to a second fluid upon cessation of feed of a first fluid.

Another object of the present invention is to provide an improved apparatus for intravenously feeding a fluid medication to a patient where, once the fluid medication is substantially administered, the system will automatically switch to an I.V. fluid flow without the attendance of a nurse or other medical personnel.

Yet another object of the present invention is to provide a novel disposable apparatus for the intravenous administration of fluid medication followed by I.V. fluid.

Still further, another object of the present invention is to provide an improved disposable tubular feeding apparatus.

Yet another object of the present invention is to provide an improved method for the tubular feeding of a first fluid, such as a liquid medication, with automatic switching to a second fluid, such as an I.V. fluid, upon substantial completion of administration of the medication, the respective fluids being administered at the same or different rates.

Generally speaking, the apparatus of the present invention relates to a system for tubular administration of medication or other first fluid with automatic switching to I.V. fluid or other second fluid flow when the first fluid administration is substantially complete comprising a first reservoir for dispensing said first fluid, said reservoir having adjustable flow discharge means connected thereto, said reservoir being adapted for connection to a source of first fluid; a second reservoir for dispensing a second fluid, said second reservoir being in communication with said first reservoir and having a variable volumetric capacity, whereby said second reservoir may be adjusted to contain a volume of a second fluid less than the volume of the first fluid contained in said first reservoir, said second reservoir having overflow, adjustable discharge means associated with an upper portion of same, said second reservoir being adapted for connection to a source of second fluid, said discharge means from both reservoirs being associable with a common intravenous or other tubular feed means; and vent means for opening and closing said reservoirs to the atmosphere, whereby once a predetermined amount of said first fluid is located within said first reservoir and said second reservoir is preset to a volumetric capacity slightly less than the volume of said first fluid, flow from the source of said second fluid will cause the first fluid to discharge and will fill the second reservoir, the second reservoir overflowing into said overflow discharge means just prior to completion of administration of said first fluid to prevent air from entering the system and/or to prevent clotting at the point of administration into the patient.

More specifically, the apparatus of the present invention includes a pair of reservoirs, preferably both having a variable volumetric capacity with means to adjust the capacities to predetermined amounts, whereby the volumetric capacity of the second reservoir is slightly less, preferably around three milliliters, than the volumetric capacity of the first reservoir. The two reservoirs are in communication with each other whereby once the lines leading from the reservoirs to the feed means assembly are purged and the flow rates for each reservoir is independently set as desired, the second fluid flowing into the second reservoir will displace air into the first reservoir and will assist in feeding the first fluid into the patient. Once the volumetric capacity of the second reservoir is reached, at a point slightly less than the total volume of the first fluid, the second reservoir fluid will overflow into an overflow discharge means, preferably located adjacent an upper end of said second reservoir whereupon fluid entering the overflow discharge means will open a valve, preferably a floating ball valve and permit discharge of the second fluid. By the time the overflow causes opening of the ball valve and feeding of the second fluid begins, the first fluid has been substantially completely administered.

In a most preferred embodiment, both the first and second reservoirs are provided with plunger systems that may be moved up and down therein such that the volumetric capacities of the two reservoirs are variable and may be set by moving the two plungers to a particular point. When the plungers are interconnected for simultaneous movement, the second reservoir will always hold slightly less fluid than the first reservoir which ensures overflow discharge into the overflow discharge means associated with the second reservoir prior to completion of administration of the first fluid. The apparatus of the present invention may be manufactured for disposal after use with a single patient. A unit may thus be produced to include the two reservoirs plus the overflow discharge chamber with each of the reservoirs being adapted for connection to a container of fluid and with the first reservoir being adapted for connection to a flow rate discharge means and the overflow discharge means of the second reservoir being adapted for connection to a similar system with both of the flow rate discharge means joining at a wye connection which is adapted for connection to a feed means via a leur adaptor or the like, or with the feed means being a part of same.

DESCRIPTION OF THE PREFERRED EMBODIMENTS

Figure 1:
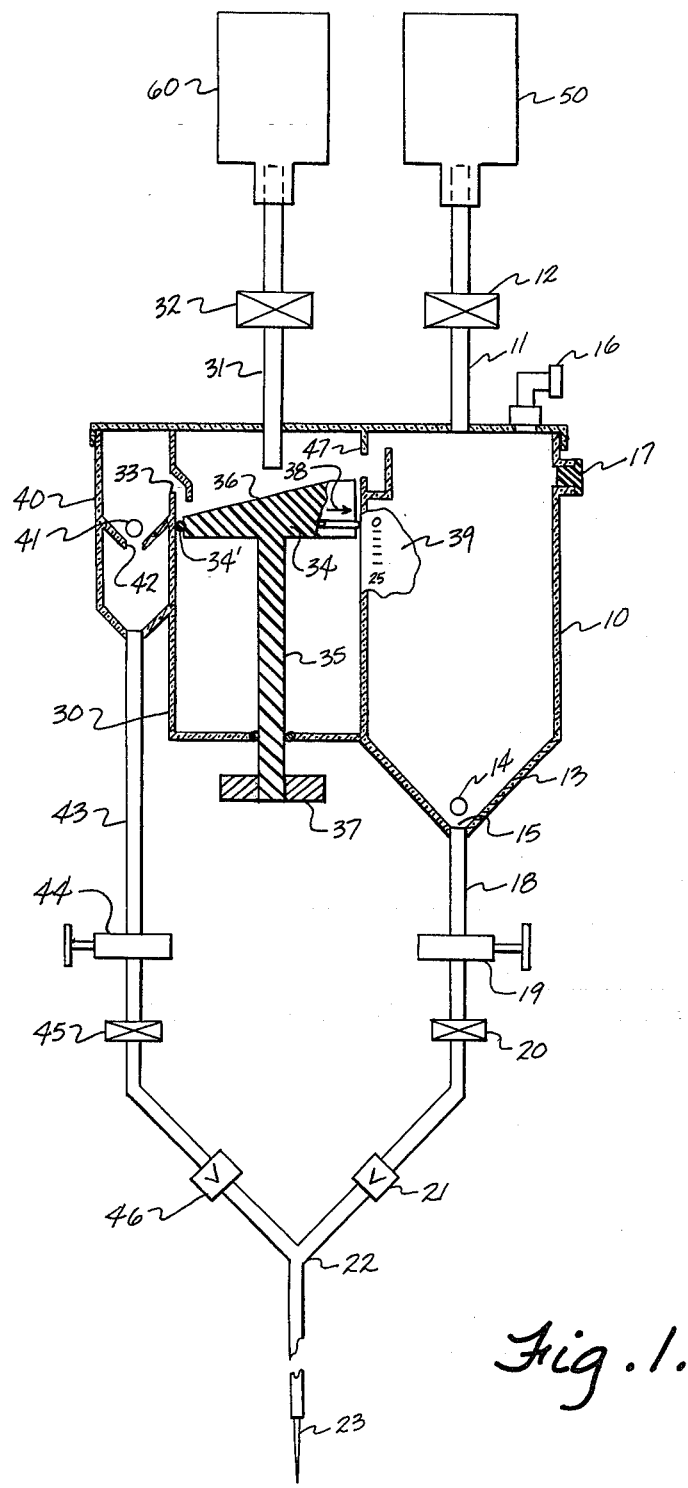
FIG. 1 is a schematic elevational view in partial cross section of an automatic tubular feeding apparatus according to teachings of the present invention.

Making reference to the Figures, preferred embodiments of the present invention will now be described in detail. As referred to herein, tubular feeding or administration refers primarily to intravenous feeding, though any other technique is included where the fluid is fed into a patient or body organ by way of a tube having a cannula, catheter, needle or other feed means in conjunction therewith. FIG. 1 illustrates one particular embodiment of an automatic intravenous feed apparatus according to teachings of the present invention which includes a first reservoir 10 into which medication or some other fluid is fed for intravenous or other administration to a patient. First reservoir 10 has a connection 11 with a valve means 12 located therein to which a source of solution 50 may be connected. A sloped bottom 13 is provided for dispensing of liquid medication from reservoir 10 along which a ball valve 14 is located to be seated at an appropriate seat 15. When fluid is present within reservoir 10, ball 14 will float off seat 15, and conversely as fluid leaves reservoir 10, ball 14 will move in the direction of seat 15 and will ultimately come to rest thereon to close off reservoir 10. Medication solution being discharged from reservoir 10 passes via conduit 18, needle valve 19 which is provided to permit accurate adjustment of the flow rate, an off-on valve 20, a check valve 21 and through wye connection 22 to cannula assembly 23 for infusion into the patient. Reservoir 10 is also provided with a venting means 16 and a medication add port means 17.

Second reservoir 30 is provided with a tube 31 and valve 32 for connection to a source of I.V. solution 60 or other second fluid. Reservoir 30 has a movable wall 34 received therein for varying the capacity of same, wall 34 preferably being a plunger where the wall 34 is the head to which a stem 35 is connected with stem 35 extending through the bottom wall of reservoir 30 and having a handle means 37 at a terminal end of same to permit manipulation of wall 34 to an appropriate position where an indicator 38 corresponds with indicia 39 that specifies the capacity of first reservoir 10. Movable wall 34 has a sloped upper surface 36, the purpose of which will be described hereinafter and has means 34' thereon to make sealing engagement with the interior of walls of reservoir 30 to preclude the passage of fluid below wall 34 in whatever position wall 34 may be set within reservoir 30.

Reservoir 30 has an overflow discharge opening 33 adjacent an upper end of same which communicates reservoir 30 with a discharge chamber 40 in which a floating ball valve is provided having a floating ball 41 and a seat 42. Discharge chamber 40 is connected to a discharge conduit 43 in which there is an adjustable needle valve 44, an off-on valve 45 and a check valve 46 which lead into wye connection 22 and thus to cannula assembly 23. Second reservoir 30 communicates with first reservoir 10 via a port 47 located adjacent the upper ends of same.

Figure 2:
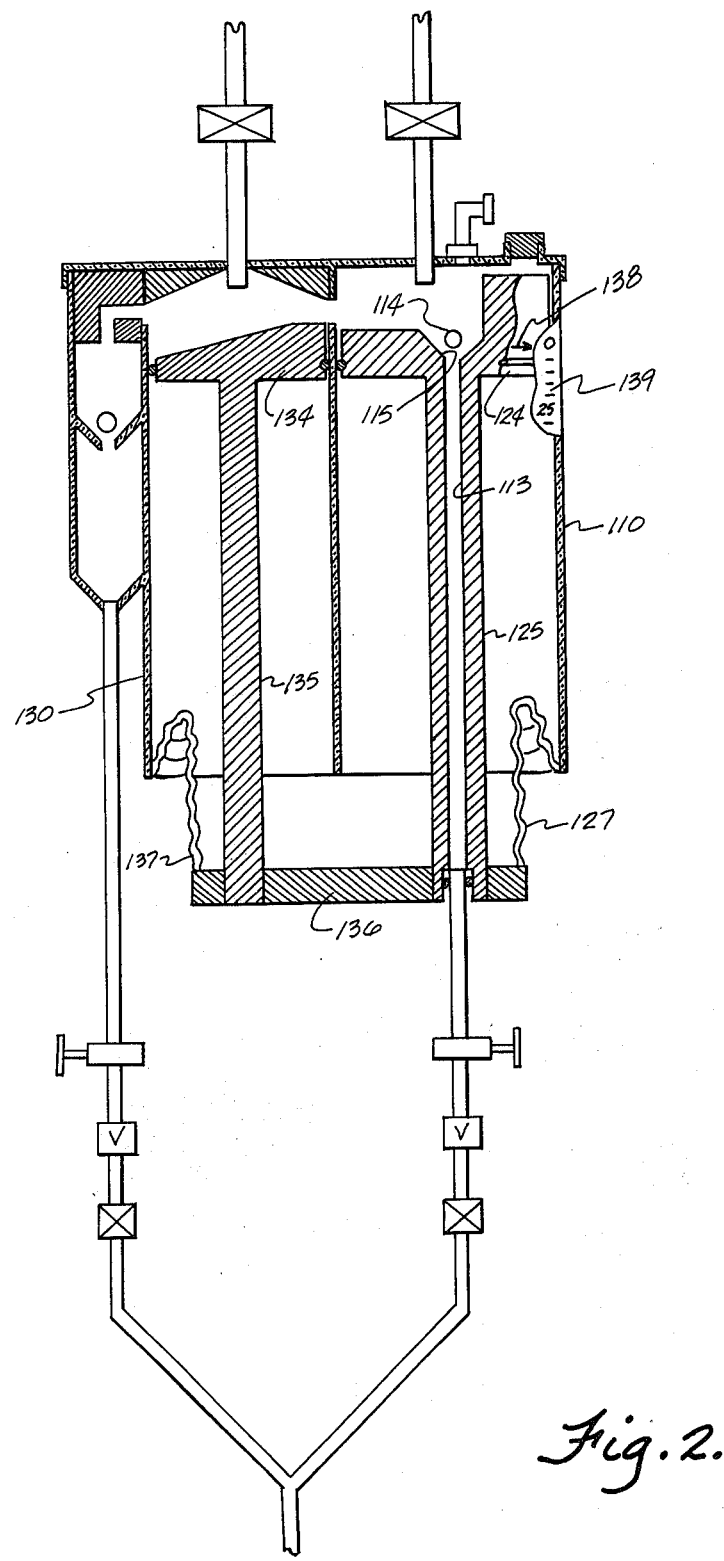
FIG. 2 is a further schematic view in partial cross section of a further apparatus embodiment according to teachings of the present invention.

FIG. 2 illustrates a further embodiment of the automatic intravenous apparatus according to teachings of the present invention which includes a first reservoir 110 and a second reservoir 130 that are generally arranged as described in FIG. 1 with the following exceptions. Both reservoirs 110 and 130 have movable walls 124 and 134, respectively, to which shafts 125 and 135, respectively, are connected which terminate in a handle member 136 which serves as a portion of the bottom wall of each respective reservoir. Movable walls 124 and 134 are thus connected by handle means 136 and each reservoir has a flexible sleeve 127 and 137, respectively, which expands with a downward movement of movable walls 124 and 134 to prevent contamination of the plungers.

In FIG. 2 as opposed to FIG. 1, the discharge opening 113 is defined by movable wall 124 and shaft 125 with a ball valve seat 115 provided in movable wall 124 to receive a floating ball 114. Further, movement of handle means 126 causes movable walls 124 and 134 to move simultaneously by a like amount whereby an indicator 138 moves along indicia 139 on a portion of reservoir 110, though same could be provided on reservoir 130, so that the appropriate amount of medication may be infused. As with FIG. 1, reservoir 130 at any setting is slightly less in volumetric capacity than reservoir 110 to permit the automatic switching from medication to I.V. solution as will be discussed in detail hereinafter.

Figure 3:
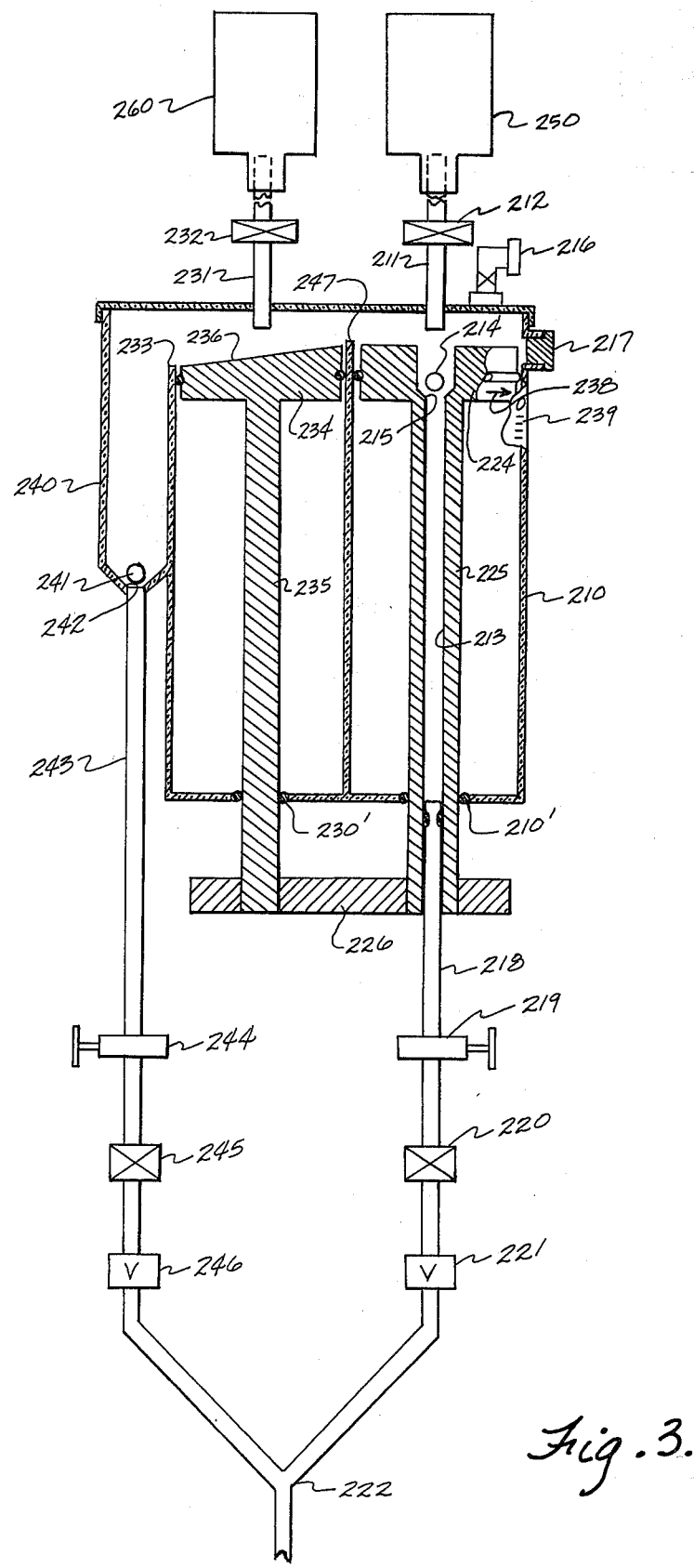
FIG. 3 is a schematic view in partial cross section of yet a further, and most preferred embodiment of automatic tubular feeding apparatus according to teachings of the present invention.

FIG. 3 illustrates a most preferred embodiment of the present invention and particulars of operation of the method and apparatus according to teachings of the present invention will be described hereinafter with respect thereto, understanding that the general method of operation for all three embodiments is basically the same.

In FIG. 3, the apparatus includes a first reservoir 210 into which a fluid medication or other first fluid is to be provided for intravenous or other feeding to a patient. First reservoir 210 has a connector 211 with a valve 212 therein for connection to a source of first solution 250. Additionally, first reservoir 210 is provided with a movable wall 224 having a shaft 225 and a handle means 226 connected thereto while a second reservoir 230 likewise has a movable wall 234 with a shaft 235 connected to the handle means 226 so as to unify the two plungers or movable wall members 224 and 234, whereby regardless of the position of the plunger handle means 226, the respective positions of walls 224 and 234 provide the relative volumetric capacities of first reservoir 210 and second reservoir 230 such that the apparatus of the present invention will function in its intended manner. First reservoir 210 has a discharge outlet 213 that is defined centrally of movable wall 224 and shaft 225 with a floating ball valve 214 being provided to seat in an appropriately designed housing 215 within movable wall 224. Shafts 225 and 235 are received in an appropriately sealed opening 210' and 230' of reservoirs 210 and 230, respectively, with an appropriate sliding seal connection being provided between discharge opening 213 and discharge conduit 218. Along discharge conduit 218 from reservoir 210 is an adjustable needle valve 219, an off-on valve 220, and a check valve 221 which lead to wye connection 222.

Second reservoir 230 is provided with an in feed conduit 231 having a valve 232 therein that is adapted for connection to a source of I.V. or other second fluid 260. Likewise, second reservoir 230 has a discharge opening 233 adjacent an upper end of same which communicates with a discharge chamber 240 in which a floating ball 241 is provided that floats in the presence of fluid and comes to rest in the absence of fluid on a seat 242 to seal off discharge chamber 240. Discharge chamber 240 is further provided with a discharge conduit 243 that leads to wye connection 222 and has disposed along the length of same, a needle valve 244, an off-on valve 245 and a check valve 246. Furthermore, as with the embodiment shown in FIGS. 1 and 2, a communication port 247 is provided between first reservoir 210 and second reservoir 230. Likewise, a cannula assembly (not shown) would be connected to wye connection 222 to permit the intravenous feeding of the first or second fluid to the patient.

Referring to FIG. 3, the operation of the apparatus and the method according to teachings of the present invention will now be described in detail with respect to the intravenous feeding of a liquid medication followed by an automatic switching to an I.V. type fluid. With the apparatus as set up in FIG. 3, all valves would initially be closed. The following is a step-by-step sequence of use of the apparatus of the present invention and the general steps of the method.

Step 1. Open valves 232, 244 and 245, whereby I.V. fluid will flow from the supply 260 through conduit 231 passing off sloped wall 236 of movable wall 234 through discharge opening 233 into discharge chamber 240 whereby ball 241 in chamber 240 will float off its seat 242, permitting fluid discharge through conduit 243, needle valve 244, on-off valve 245 and wye connection 222 to the cannula assembly (not shown). This step is performed to purge the I.V. fluid discharge line of any air and initial adjustment of needle valve 244 is made for a desired rate of feed of the I.V. fluid.

Step 2. Valves 232 and 245 are closed and valves 212, 219 and 220 opened. Solution 250 feeds into reservoir 210 and floats ball 214 off its seat 215, permitting fluid flow through discharge opening 213 into conduit 218 and on to wye connection 222. With the fluid continuing to flow, needle valve 219 is adjusted to achieve an initial rate of flow from medication reservoir 210. Valves 212 and 220 are then closed.

Step 3. Now that the discharge lines from reservoirs 210 and 230 have been purged and contain fluid, valves 232 and 245 are reopened to permit I.V. fluid to flow into discharge chamber 240 whereupon needle valve 244 may be precisely adjusted to achieve a desired I.V. flow.

Step 4. Valves 232 and 245 are again closed and valves 212 and 220 reopened to permit needle valve 219 to be precisely adjusted to the exact rate of flow. Valves 212 and 220 are then closed. Obviously, the flow rates from reservoirs 210 and 230 may be the same or different as desired.

Step 5. With inlet valves 212 and 232 closed and discharge valves 220 and 245 closed, vent 216 is opened and movable walls 224 and 234 moved down to the desired level by pulling on plunger handle 226, whereby the desired capacity of medication reservoir 210 is indicated by pointer 238 along indicia 239 with second reservoir 230 being preset to a volumetric capacity slightly less than reservoir 210, i.e., approximately three milliliters.

Step 6. With the apparatus set as described in Step 5, medication is added through the port 217 by a syringe or the like to deposit the precise amount of medication into reservoir 210. Thereafter, solution 250 is added to reservoir 210 by opening valve 212 while the vent remains open, whereby reservoir 210 may be filled to the zero line on indicia 239 to provide a precise amount of solution and medication in reservoir 210 which may then be appropriately mixed.

Step 7. Vent 216 is closed, solution addition valve 212 is closed, I.V. fluid valve 232 is opened and discharge valves 220 and 245 are opened. With reservoirs 210 and 230 preset to their respective volumetric capacities, with ball valve 214 floating in the medication solution and with ball valve 241 resting on its seat 242 in discharge chamber 240, I.V. fluid will be introduced into reservoir 230 and displace air therefrom into reservoir 210 via port 247 and cause the medication solution to feed from reservoir 210 through discharge conduit 218, wye connection 222 and the cannula assembly, into the patient. As I.V. fluid continues to accumulate in reservoir 230 and displaces air into reservoir 210, ball 214 follows the flow of medication solution and continues to approach its seat 215. Just prior to ball 214 becoming seated at seat 215 to seal reservoir 210 from further discharge, I.V. fluid overflows through discharge port 233 into discharge chamber 240, all due to the lesser volumetric capacity of reservoir 230 when compared to reservoir 210. The I.V. fluid overflow causes ball 241 to float off its seat 242 whereby I.V. fluid is being prepared for automatic switching. As ball 214 rests on seat 215 and precludes further discharge from reservoir 210, ball 241 in discharge chamber 240 has floated away from its seat 242 and I.V. fluid begins to automatically flow through conduit 243, wye connection 222 and the cannula assembly into the patient.

The automatic switching from medication to I.V. fluid accomplishes several purposes. First, it precludes air from being introduced into the discharge lines. Secondly, a continuation of flow through cannula assembly 223 will prevent clotting of the patient's blood within cannula assembly 223 such that the apparatus of the present invention may be left in place, that is, with cannula assembly 223 taped to the patient's body and I.V. fluid or the like may be continually fed therethrough until the next occasion when it is desired to intravenously feed medication to the patient.

Following use of the apparatus, should it be desirable to reinstitute the feeding of medication to a patient, with the I.V. fluid inlet valve 232 open and the remainder of the valves closed, the movable walls may be returned to their original position, whereby any I.V. fluid remaining in the second reservoir will be returned to its source.

Apparatus according to teachings of the present invention may be conveniently manufactured for marketing as a disposable item. Each figure illustrates the reservoirs to have a removable top and with the movable walls, stems and handles shown in more than one piece. Such is generally illustrated as one approach to fabrication of the apparatus. Obviously one skilled in the art could readily ascertain numerous other ways of fabrication of the apparatus.

Preferably apparatus according to the present invention could include a reservoir unit molded of a synthetic polymeric material with the movable wall assembly and balls in place. Means would be provided adapted for connection to the two sources of fluid along with valved discharge conduits united at a wye connection. Conduit leading from the wye connection could then be coupled to any conventional cannula, catheter, needle or other feed means by way of a leur adaptor, for example. Alternatively, only the reservoir units with discharge means could be manufactured in the disposable unit with the valved discharge conduits, etc., being separately provided. Further, while the present invention has been described with reference to a fluid medication followed by automatic switching to an I.V. fluid, obviously any two same or separate fluids may be utilized with the apparatus of the present invention.

Apparatus according to teachings of the present invention provides definite improvement over known systems. No power connectors, timers, magnetic or mechanical valves, batteries or springs are required, yet the system performs in virtually a fail-safe manner to achieve intended results.

Having described the present invention in detail, it is obvious that one skilled in the art will be able to make variations and modifications thereto without departing from the scope of the invention. Accordingly, the scope of the present invention should be determined only by the claims appended hereto.

That which is claimed is:

1. A system for tubular administration of a first medical solution with automatic conversion to administration of a second medical solution when administration of the first medical solution is substantially complete comprising:
   (a) a housing;
   (b) a first reservoir located in said housing and being adapted to receive a predetermined quantity of said first solution, said reservoir having floating ball valve means associated therewith that automatically open in the presence of a quantity of said first solution and close in the absence of first solution, said first reservoir means further being associated with solution discharge means;
   (c) a second reservoir located in said housing in communication with said first reservoir, said second reservoir having a wall movable therein to preset the volumetric capacity thereof at a volume less than the volume of first solution to be received in said first reservoir, said second reservoir further having an overflow chamber in communication therewith, said overflow chamber having floating ball valve means associated therewith, said valve means opening in the presence of a quantity of said second solution and closing in the absence of second solution, said overflow chamber valve means being associated with solution discharge means and said second reservoir being adapted for association with a source of second solution, both said solution discharge means being connectable with a means for feeding said solutions to the body of a patient, said effective volumetric capacity of said second reservoir being such that second solution flowing into said chamber during feeding of first solution from said first reservoir will overflow into said overflow chamber just prior to completion of discharge of said first solution, whereby second solution discharge from said second reservoir automatically initiates without height dependence of said first or second solution.

2. The automatic system as defined in claim 1 wherein a top surface of the movable wall is sloped in the direction of the overflow chamber associated with said second reservoir.

3. The automatic system as defined in claim 1 wherein the solution discharge means associated with both reservoirs comprise an adjustable flow rate valve means, an off-on valve means and a check valve means.

4. The automatic system as defined in claim 1 wherein the first reservoir solution discharge means is associated with a lower end of same, said lower end having said floating ball valve means located therein.

5. The automatic system as defined in claim 1 wherein said first reservoir has atmospheric venting means associated therewith.

6. The automatic system as defined in claim 1 wherein both reservoirs have movable walls received therein for predetermining the respective volumetric capacities of same.

7. The automatic system as defined in claim 6 wherein both reservoirs include an expandable bottom portion to protect said movable walls from contamination.

8. The automatic system as defined in claim 1 wherein both reservoirs have movable walls received therein for predetermining the respective volumetric capacities of same, said movable walls being associated such that the effective volumetric capacity of said second reservoir is preset for each volumetric setting for said first reservoir, the movable wall in said first reservoir defining a passageway therethrough and having the solution discharge means associable therewith, said first reservoir valve means being associated with said passageway defined by said movable wall.

9. A system for tubular administration of a medication solution with automatic conversion to administration of an I.V. solution when said medication administration is substantially complete comprising:
(a) a first reservoir for mixing and dispensing medication solution, said reservoir being adapted for receiving medicine and a solution carrier for said medicine, said reservoir further being adapted to receive a predetermined volume of medication solution, said reservoir having, automatic opening and closing discharge means at a lower end of same;
(b) a second reservoir for dispensing an I.V. solution, said second reservoir being in communication with said first reservoir adjacent an upper end of same and being adapted for connection to a source of I.V. solution, said second reservoir having an overflow chamber means located along a side wall of same, said overflow chamber means having automatic opening and closing discharge means adjacent a lower end of same, one of said reservoirs having atmospheric venting means associated therewith, said second reservoir having a movable wall receivable therein to adapt said second reservoir to contain a lesser volume of said second solution than the volume of said first solution in said first reservoir such that said second reservoir overflows into said overflow chamber means just prior to completion of discharge of said first solution from said first reservoir to automatically initiate feeding of said second solution upon completion of feeding of said first solution; and
(c) a wye connecton connected to both said discharge means, said wye connection being connectable to a tubular feed means.

10. The automatic system as defined in claim 9 wherein each reservoir has a movable wall located therein, said walls being movable within said reservoirs to define a predetermined volumetric capacity in each reservoir above the said wall.

11. The automatic system as defined in claim 10, wherein the movable walls in the first and second reservoirs are connected, whereby adjustment of the volumetric capacity of one of the reservoirs automatically determines the volumetric capacity of the other reservoir.

12. The automatic system as defined in claim 11 wherein the plunger in the first reservoir defines a discharge passageway therethrough, said passageway being in communication with said first reservoir solution discharge means which includes a floating ball valve means located along said passageway, said valve means automatically opening in the presence of a quantity of first solution and closing in the absence of first solution.

13. The automatic system as defined in claim 11 wherein said movable walls are connected for simultaneous adjustment of the respective volumetric capacities of both said reservoirs, said movable wall in said first reservoir defining a solution discharge passageway therein and wherein solution discharge means for both reservoirs comprise a floating ball valve, adjustable flow rate valve means, off-on valve means and check valve means, the floating valve means for said first reservoir being located along said passageway defined by said movable wall and the floating ball valve means for said second reservoir being located in said overflow chamber.

14. The automatic system as defined in claim 13 wherein at least one reservoir is provided with volume indicia adjacent the path of movement of the movable wall.

15. The automatic system as defined in claim 9 wherein said atmospheric venting means are associated with said first reservoir.

16. A method for tubular administration of a first solution with automatic conversion to a second solution when administration of the first solution is substantially complete comprising the steps of:
(a) providing a predetermined quantity of first solution in a first reservoir, said first reservoir having automatic opening and closing valve means associated therewith, said valve means being further associated with a solution discharge means and a tubular feed means;
(b) providing a second reservoir in communication with said first reservoir, said second reservoir having a volumetric capacity slightly less than the amount of first solution in said first reservoir, said second reservoir having an overflow chamber associated therewith, said overflow chamber having automatic opening and closing valve means associated with a solution discharge means and said tubular feed means; and
(c) supplying a second solution into said second reservoir while said both discharge means are opened, the valve means of said first reservoir is open, the valve means of said overflow chamber is closed and both reservoirs are closed to the atmosphere, whereby incoming second solution displaces air from said second reservoir into said first reservoir to assist in discharging said first solution therefrom until said second reservoir is full, after which second solution fluid will overflow into said overflow chamber and automatically open said valve means associated therewith and will be fed to a patient without interruption upon substantial completion of administration of said first solution, and said valve means associated with said first reservoir closes as administration of said first solution is being completed.

17. The method as defined in claim 16 wherein the self opening and closing valve means for the first and second reservoirs are floating ball valve means in which the ball floats in the presence of adequate solution to open the valve means and reseats in the absence of adequate solution to close the valve means.

18. The method as defined in claim 16 wherein before introduction of the predetermined quantity of first solution into the first reservoir, the discharge means from the first and second reservoirs are purged to remove any air from the lines and are left full of solution.

19. The method as defined in claim 18 comprising the further step of adjusting the flow rate from each reservoir prior to providing said first and second solutions.

20. The method as defined in claim 16 wherein each reservoir is equipped with a movable wall means that is movable along the reservoir to determine the volumetric capacity of each reservoir, said movable walls having been preset prior to introduction of the predetermined quantity of first solution into said first reservoir.

21. The method as defined in claim 20 wherein both walls are connected whereby movement of same always maintains a volumetric capacity in the second reservoir slightly less than the volumetric capacity of the first reservoir.

22. The method as defined in claim 21 wherein the volumetric capacity of the second reservoir is always approximately three milliliters less than the volumetric capacity of the first reservoir.

23. An automatic system for use in sequential intravenous administration of first and second solutions comprising:
   (a) a housing, said housing defining a first reservoir having a movable wall therewithin and having an automatically opening and closing valve means, a second reservoir adjacent said first reservoir, a movable wall received within said second reservoir, said walls being movable within said respective reservoirs to determine the volumetric capacity of said reservoirs, whereby said second reservoir can be preset to a volumetric capacity less than the volumetric capacity of said first reservoir when in use, said second reservoir being in communication with said first reservoir adjacent an upper end of same and an overflow chamber located adjacent said second reservoir and being in communication with said second reservoir to receive solution overflow from said second reservoir just prior to completion of solution discharge from said first reservoir, said overflow chamber having automatically opening and closing valve means, said reservoirs being adapted for connection to a source of solution;
   (b) separate solution discharge means associated with said first reservoir and said overflow chamber; and
   (c) a common infusion feed assembly associated with both solution discharge means.

24. The system as defined in claim 23 wherein said walls are connected outside said reservoirs whereby said walls may be moved simultaneously to adjust the capacities of said reservoirs.

25. The system as defined in claim 23 wherein said overflow chamber is integral with said housing and wherein said automatically opening and closing valve means are ball valve means.

26. The system as defined in claim 25 wherein both said solution discharge means comprises an adjustable flow rate valve means, an on-off valve means and a check valve means, both said discharge means being associated with a wye connection.

27. The system as defined in claim 25 wherein said housing further comprises a movable wall received in each reservoir, said walls having stems extending downwardly therefrom and terminating at a common handle means, the position of said walls within said reservoirs determining the volumetric capacities of said reservoir, and wherein said wall and stem within said first reservoir define a solution discharge opening therein, said ball valve means being located thereat.

* * * * *